United States Patent [19]

Suzuki et al.

[11] Patent Number: 5,015,091

[45] Date of Patent: May 14, 1991

[54] DEVICE FOR DETECTING ALCOHOLIC CONTENT

[75] Inventors: Hiroyoshi Suzuki; Kenji Ogawa; Hiroko Maekawa, all of Himeji, Japan

[73] Assignee: Mitsubishi Denki K.K., Tokyo, Japan

[21] Appl. No.: 327,059

[22] Filed: Mar. 22, 1989

[30] Foreign Application Priority Data

Apr. 13, 1988 [JP] Japan ................................. 63-92164
Apr. 14, 1988 [JP] Japan ................................. 63-93938

[51] Int. Cl.$^5$ ............................................. G01N 21/41
[52] U.S. Cl. .................................................. 356/135
[58] Field of Search ............... 356/128, 130, 133, 134, 356/135, 137, 136

[56] References Cited

U.S. PATENT DOCUMENTS

| 2,483,102 | 9/1949 | Pierson | 356/134 |
|---|---|---|---|
| 3,267,795 | 8/1966 | Goldberg | 356/137 |
| 3,299,770 | 1/1967 | Witt et al. | 356/133 |
| 3,384,885 | 5/1968 | Forbush | 356/133 |
| 3,426,211 | 2/1969 | Anderson | 356/135 |
| 3,932,038 | 1/1976 | Schweizer et al. | 356/133 |
| 4,641,965 | 2/1987 | Harmer | 356/135 |
| 4,650,323 | 3/1987 | Nakagawa | 356/135 |
| 4,749,274 | 6/1988 | Aoki et al. | 356/136 |

FOREIGN PATENT DOCUMENTS

| 3726886 | 3/1988 | Fed. Rep. of Germany. | |
| 39171 | 4/1975 | Japan. | |
| 51920 | 3/1982 | Japan. | |
| 129235 | 8/1983 | Japan | 356/128 |
| 201236 | 10/1985 | Japan | 356/128 |
| 757944 | 8/1980 | U.S.S.R. | 356/135 |
| 928203 | 5/1982 | U.S.S.R. | 356/128 |

Primary Examiner—Richard A. Rosenberger
Attorney, Agent, or Firm—Sughrue, Mion, Zinn, Macpeak & Seas

[57] ABSTRACT

The present invention is directed to a device for detecting alcoholic content in a fuel by finding its refractive index, which is of such a construction that a refractive interface for the fuel is formed at an intermediate portion of a light transmission body; a light emitting element is provided at one end of the light transmission body, from which incident light is introduced into said refractive interface; and a single dimensional light position sensing detector is provided at the other end of the light transmitting body, into which the light refracted at the refractive interface is introduced. Alternatively, the device is of such a construction that a light emitting element and a single dimensional light position sensing detector are provided at one end of a light transmission body; a refractive interface and a reflecting surface are provided at the other end of the light transmission body, wherein an incident light from the light emitting element, which has entered into the refractive interface and has been refracted there, is reflected at the reflecting surface, after which the reflected light is again caused to enter into the refractive interface, and is subsequently caused to enter into the single dimensional light position sensing detector.

4 Claims, 8 Drawing Sheets

DEVICE FOR DETECTING ALCOHOLIC CONTENT

The present invention relates to a device for determining the nature of fuels to be supplied to burners or the like in a non-contact manner. More particularly, it is concerned with a device for measuring the alcoholic content in fuels to be used for internal combustion engines of automobiles, etc., containing therein alcohol in mixture.

In recent years, the U.S.A. and various European countries have adopted, as an automobile fuel, a mixed fuel containing alcohol in gasoline for the purpose of reducing consumption of petroleum, and such fuel is being diffused guradually among consumers. However, when such alcohol-mixed fuel is used, as it is, in those combustion engines originally matched with the air-fuel ratio of the fuel gasoline, there occurs a leaning phenomenon due to the fact that alcohol has a smaller theoretical air-fuel ratio than that of gasoline, and other facts. On account of this, it becomes necessary to regulate the air-fuel ratio, the ignition timing of the engine, and so forth in accordance with the alcoholic content in the fuel by controlling an actuator such as fuel injector, etc. through detection of the alcoholic content in the alcohol-mixed fuel. As the device for detecting the alcoholic content in the fuel such as mentioned above, there has so far been known one as described in, for example, unexamined Japanese Patent Publication No. 51920/1982. This device will be explained hereinbelow in reference to FIGS. 12 and 13 of the accompanying drawing.

FIG. 12 is a schematic structural diagram of a fuel control system provided with a conventional device for detecting the alcoholic content, in which a reference letter A denotes an alcoholic content detector, a reference numeral 20 designates an internal combustion engine, a numeral 21 refers to a fuel injector, a reference numeral 22 represents a fuel tank, and a numeral 23 refers to a fuel pump which is connected with a high pressure filter 25 through a fuel supply pipe 24. A reference numeral 26 designates a fuel distribution pipe for the above-mentioned fuel injector 21, a numeral 27 refers to a fuel pressure regulator, and a numeral 28 refers to a fuel return pipe which is led into the fuel tank 22. A reference numeral 29 designates a sensor for air-fuel ratio, a numeral 30 refers to an ignition plug, a reference numeral 31 represents a engine speed sensor, a reference numeral 32 indicates a sensor for intake air pressure, a reference numeral 33 denotes a throttle valve, and a numeral 34 refers to an air cleaner. A reference numeral 35 designates a control device, into which are introduced input signals from the alcoholic content detector A, the air-fuel ratio sensor 29, the engine speed sensor 31 and the intake air sensor 32, both of which represent quantities of the state of engine, and so forth to drive the fuel injector 21 and the engine ignition plug 30 with the controlled quantities in accordance with these inputs. When the alcohol-mixed fuel is supplied to the fuel tank 22, the mixed fuel is pressurized by the fuel pump 23 with commencement of the engine operation, and introduced into the alcoholic content detector A through the fuel supply pipe 24 and the high pressure filter 25, where the alcoholic content of the fuel is measured. Thereafter, the fuel flows into the fuel distribution pipe 26 where a part of the fuel is supplied to the engine by the fuel injector 21, and remaining part thereof is returned to the fuel tank 22 by way of the fuel pressure regulator 27 and the fuel return pipe 28. The fuel pressure regulator 27 always maintain the pressure of the fuel upto the fuel distribution pipe 26 at a constant value, irrespective of the fuel injection quantity through the fuel injector 21. When the signal for the alcoholic content as measured by the alcoholic content detector A is introduced as an input into the control device 35 the state of the engine operation is determined by the control device 35 on the basis of the signals from the engine speed sensor 31, the intake air pressure sensor 32, and so on; the valve opening time of the fuel injector 21 is controlled to vary the quantity of the fuel to be fed into the engine; the air-fuel ratio is detected by the air-fuel ratio sensor 29 to control the air-fuel ratio by feedback operation so as to bring it to an intended value in conformity to the above-mentioned state of the engine operation; and the ignition timing of the engine ignition plug 30 is controlled in accordance with the state of the engine operation.

FIG. 13 shows a detailed cross-sectional view of the above-mentioned alcoholic content detector A, in which a reference numeral 1 designates a cylindrical light transmission body formed of optical glass, etc., a numeral 2 refers to a casing for the light transmission body, a numeral 3 refers to a fuel seal provided between the light transmission body 1 and the casing 2, a reference numeral 4 represents a light emitting element such as LED, etc., a reference numeral 5 denotes a light receiving element as photodiodes, a numeral 6 refers to a fuel chamber, a reference numeral 6a designates a fuel inlet port, and a reference numeral 6b indicates a fuel outlet. A reference numeral 7a denotes reflected light by a total reflector, a numeral 7b refers to refracted light, and a numeral 10 refers to a detection circuit which functions to drive the light emitting element 4 and to measure the quantity of light received by the light receiving element 5. The outer peripheral surface of the light transmission body 1 is in uniform contact with the fuel in the fuel chamber 6. Of the light rays emitted from the light emitting element 4, the light 7a having its incident angle into the boundary surface with the fuel greater than the total reflection angle $\Phi = \arcsin(N_f/N_d)$ is totally reflected to reach the light receiving element 5, while the light 7b having its incident angle smaller than the total reflection angle $\Phi$ transmits refractively in and through the fuel, on account of which the light receiving element 5 receives only those light rays, of which the incident angle into the boundary surface becomes greater than the total reflection angle $\Phi$. When the alcoholic content in the fuel changes, the refractive index of the fuel $N_f$ also changes, hence the total reflection angle $\Phi$, owing to which the light receiving quantity of the light receiving element 5 also changes. By measurement of this change in the light receiving quantity by the detection circuit 10, the alcoholic content in the fuel can be found.

This conventional alcoholic content detector, however, has its disadvantage such that, since the light emitting quantity from the light emitting element 4, sensitivity for receiving light of the light receiving element 5, and frequency for the peak sensitivity are all governed by temperature, if the temperature of the alcoholic content detector changes due to generation of heat from the engine, corresponding increase in temperature of the fuel, and others, the light receiving quantity of the light receiving element 5 also changes with the consequent inability of accurately determining the alcoholic content in the fuel. Moreover, since it is not possible, in general, to make the total reflection angle Φ to be very small from the standpoint of the restriction imposed on a refractive index Nd of the light transmission body 1, the light transmission body 1 cannot be made very short in length, hence the detector itself cannot be reduced its size, which is another problem in such a conventional detector. For these reasons, the conventional alcoholic content detector had to be arranged at a position spaced apart from the engine, which made it impossible to detect, without any delay, the alcoholic content of the fuel to actually be injected from the fuel injector 21 at the time of starting the engine, in particular. This delay in detecting the alcoholic content might apprehensively cause an undesirable situation such that, at the time of starting the engine after replenishment of a fuel having different alcoholic content from that of the existing fuel in the fuel tank, there will take place an engine starting mode, in which a difference in the alcoholic content emerges between the fuel chamber 6 interior of the alcoholic content detector A and the fuel distribution pipe 26 interior, and, in the worst the case, there would occur an inconvenience such that the engine cannot start its operation at all.

The present invention has been made with a view toward eliminating the problem as mentioned above, and aims at providing an alcoholic content detector of a small size which is capable of constantly and accurately detecting the alcoholic content in the fuel without any delay and in a continuous manner, irrespective of changes in temperature thereof the device.

According to the present invention, in one aspect of there is provided a device for detecting alcoholic content in a fuel by finding its refractive index, characterized in that a refractive interface for the fuel is formed at an intermediate portion of a light transmission body; a light emitting element is provided at one end of the light transmission body, from which incident light is introduced into the refractive interface; and a single dimensional light position sensing detector is provided at the other end of the light transmission body, into which the light refracted at the refractive interface is introduced.

According to the present invention, in another aspect thereof, there is provided a device for detecting alcoholic content in a fuel by finding its refractive index, characterized in that a light emitting element and a single dimensional light position sensing detector are provided at one end of a light transmission body; a refractive interface and a reflecting surface are provided at the other end of the light transmission body, wherein an incident light, which has entered into the refractive interface from the light emitting element and has been refracted there, is reflected at the reflecting surface, after which the reflected light again enters into the refractive interface, and then is caused to enter into the single dimensional light position sensing detector.

A preferred way of carrying out the present invention will be described in detail hereinbelow with reference to the accompanying drawing which illustrate specific embodiments, in which:

FIG. 4b is a cross-sectional view as seen along a line IV—IV in FIG. 4a;

Figure 1:
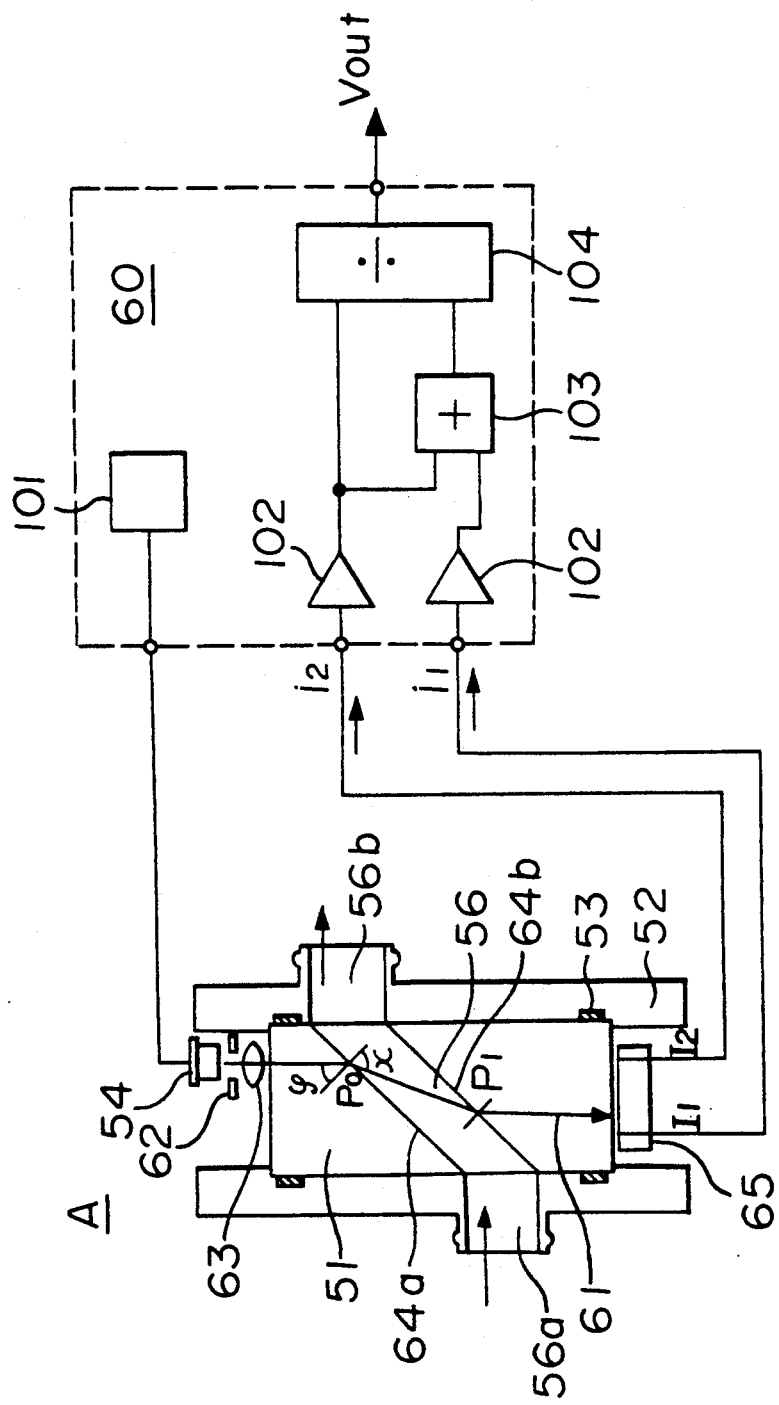
FIG. 1 is a schematic structural diagram showing an alcoholic content detector according to one embodiment of the present invention.

In the following, the present invention will be described in specific detail with reference to one preferred embodiment shown in the drawing.

Figure 13:
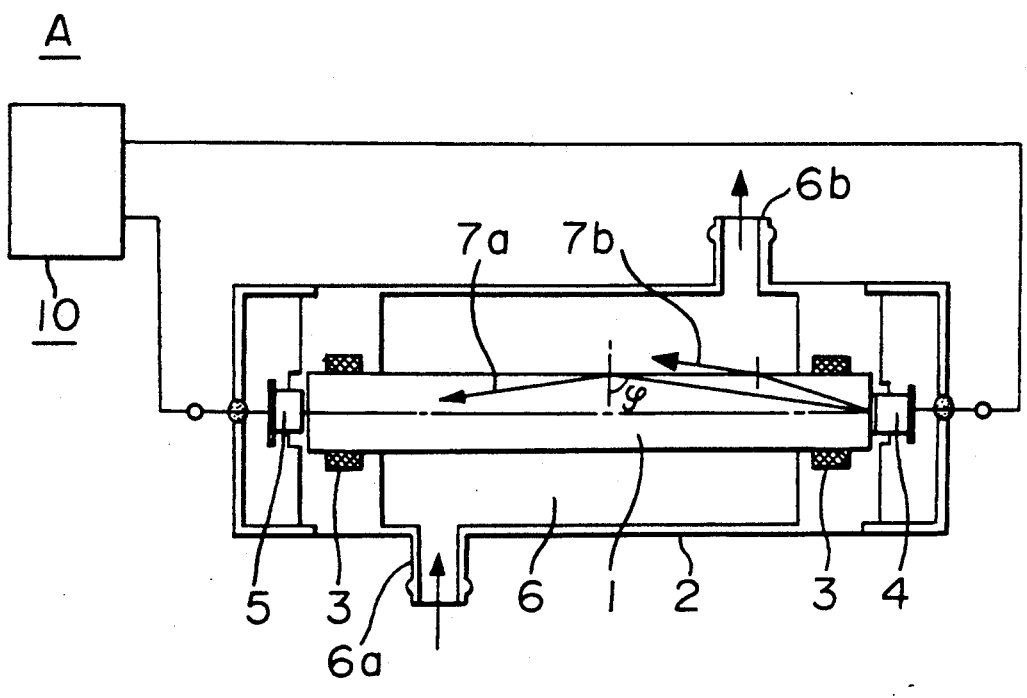
FIG. 13 is a schematic structural diagram of a conventional alcoholic content detector.

Referring first to FIG. 1 illustrating schematically the structure of the alcoholic content detector according to the present invention, a reference numeral 51 designates a columnar or cylindrical light transmission body having, in this particular embodiment, parallel planes 64a, 64b which have been formed in an intermediate part of the light transmission body at a predetermined angle with respect to the axis thereof; a numeral 56 refers to a fuel passageway formed between the above-mentioned parallel surfaces; a numeral 61 refers to light rays radiated from a light emitting element; a reference numeral 62 denotes a diaphragm; and a reference numeral 63 represents an optical lens. The parallel planes 64a, 64b constitute the refractive interface with a fuel to be detected. A reference numeral 65 designates a single dimensional light position sensing detector which is shown, in this particular embodiment, to be a semiconductor position sensing detector (hereinafter abbreviated as "PSD"). A detection circuit 60 is constructed with a constant current driving section 101 which drives the light emitting element 54, a pre-amplifier 102 for photocurrent of the PSD, an adder 103, and a divider 104. When the light emitting element 54 provided at one end of the light transmission body 51 is driven by the constant current driving section 101 and emits light, the radiated light rays 61 pass through the diaphragm 62, and, while they are being converged by the optical lens 63, enter into the fuel gasoline flowing in and through the fuel passageway 56 at a point PO of the refractive interface 64a positioned intermediate of the light transmission body 51 at an incident angle Φ. The refractive plane 64a forms a part of the fuel passageway 56 and is in contact with the fuel which has flowed into it from a fuel inlet port 56a, on account of which the incident light rays 61 are refracted at a refractive angle $x = \text{arc SIN}(Nd/Nf \times \sin \Phi)$ at the point P1 owing to a difference between the refractive index Nf of the fuel and the refractive index Nd of the light transmission body 51. The light rays which have been refracted at the refractive angle x at the point PO transmits in and through the fuel and enters at a point P1 into the refractive interface 64b which is in parallel with the above-mentioned refractive interface 64a, is further refracted in the light transmission body 51 in accordance with a relational expression between the above-mentioned incident angle $\Phi$ and the refractive angle x, and then reaches the PSD 65 disposed at the other end of the light transmission body 51. The lens 63 has its own focal length selected in such a manner that the radiated light rays 61 may be substantially collected on the PSD 65. By the way, explanations of the remaining reference numerals will be dispensed with, since they are identical with those as have already been explained in the foregoing with regard to the conventional device shown in FIG. 13.

Figure 2:
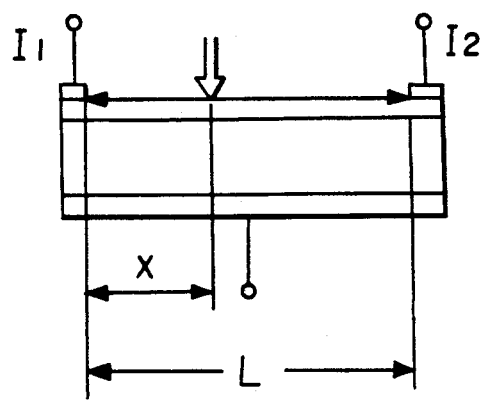
FIG. 2 is a diagram for explaining the principle of the light position detection by a light position sensing detector (PSD)

FIG. 2 is an explanatory diagram for the principle of the light position sensing by means of PSD 65. The light position sensing detector (PSD) is a detecting element for the center position of the light rays using silicon photodiodes, and is constructed with three layers, i.e., a resistance layer (P-layer), an intermediate layer, and an N-layer. When a light spot enters into this sensor, photocurrents i1 and i2 pass through the uniform resistance layer from the incident position of the light spot and flows in division into respective electrodes I1 and I2, whereby the photocurrents i1 and i2 are produced as divided outputs in inverse proportion to their distance from the respective electrodes. Assuming now that a distance from the electrode I1 to the light incident position is X and a distance between the electrodes I1 and I2 of the PSD is L, a position X is given by $X = L \times i2/(i1+i2)$. At this instance, the position X coincides with the center of the incident light, so that the diameter of the light spot need not always be made very small.

In FIG. 1, the photocurrents i1 and i2 from the respective electrodes I1 and I2 of the PSD 65 are introduced as inputs into the detection circuit 60 and amplifier by the pre-amplifier 102, after which both photocurrents i1 and i2 are added at the adder 103, and then i2 is divided by the above-mentioned result of the addition $(i2/(i1+i2))$ in the divider 104, whereby an output voltage $V_{out}$ is produced in correspondence to the position signal X. When the refractive index Nf of the fuel changes in accordance with change in the alcoholic content in the fuel, the angles of refraction at the refractive interface 64a and 64b also change, which causes the incident position X onto the PSD 65 of the radiated light rays 61 from the light emitting element 54 to change, as the consequence of which the output voltage $V_{out}$ from the detection circuit 60 takes a value commensurate with the alcoholic content.

Figure 3:
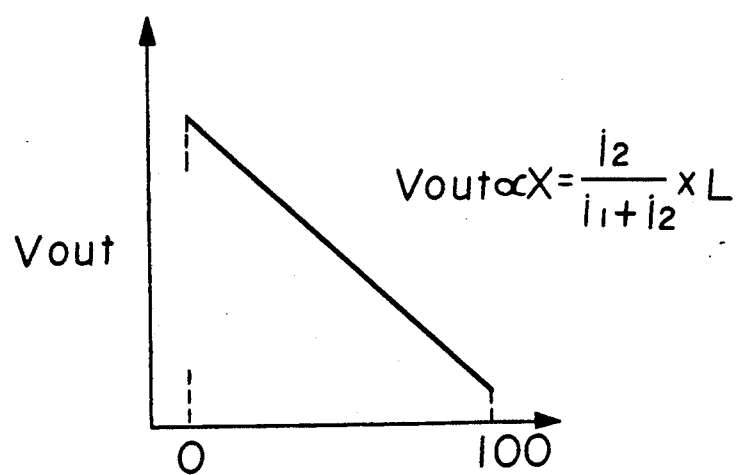
FIG. 3 is a graphical representation showing variations in an output voltage with respect to a methanol content in the fuel gasoline.

The graphical representation in FIG. 3 indicates variations in the output voltage $V_{out}$ with respect to the content of methyl alcohol in fuel gasoline in a structure of the detector using an optical glass "BK7" having its refractive index $Nd = 1.52$ as the light transmitting body 51, and with a light incident angle $\Phi = 45$ degrees. As seen from this graphical representation, since methyl alcohol has a smaller refractive index than gasoline, the light incident position onto the PSD 65 shifts to the side of the electrode I1 accordingly as the methyl alcohol content becomes greater and the photocurrent i1 becomes larger. As the result of this, the output voltage $V_{out}$ is inversely proportional to the methyl alcohol content. When the temperature of the detection device A changes due to generation of heat from the engine, corresponding elevation in temperature of the fuel due to the heat from the engine, and so forth, the light emitting quantity of the light emitting element 54 and the total photocurrent quantity of the PSD 65 vary accordingly. However, since the alcoholic content is given in terms of a ratio of the photocurrent, the alcoholic content in the fuel can always be detected accurately and continuously irrespective of the temperature variations in the detecting device A. In addition, since the alcoholic content is detected at one part of the refractive interface of the detector, the total length of the light transmission body can be shortened in comparison with that of the light transmission body used in the conventional detection device, hence the detecting part can be made advantageously small in size.

Figure 4A:
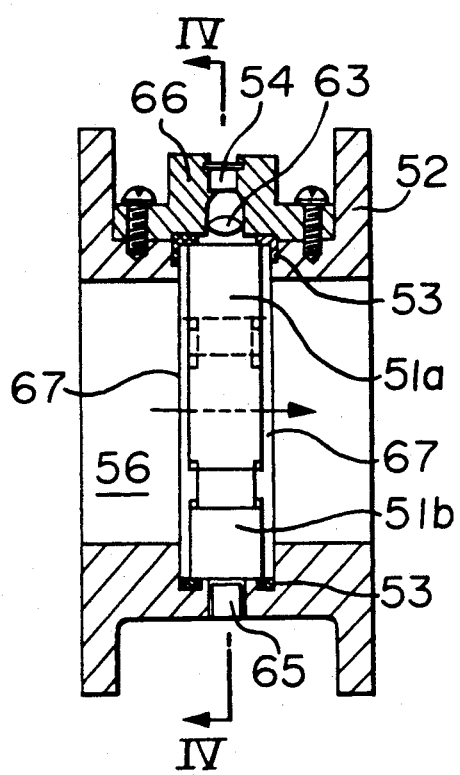
FIG. 4a is a cross-sectional view showing a sensing part of the alcoholic content detector.
Figure 4B:
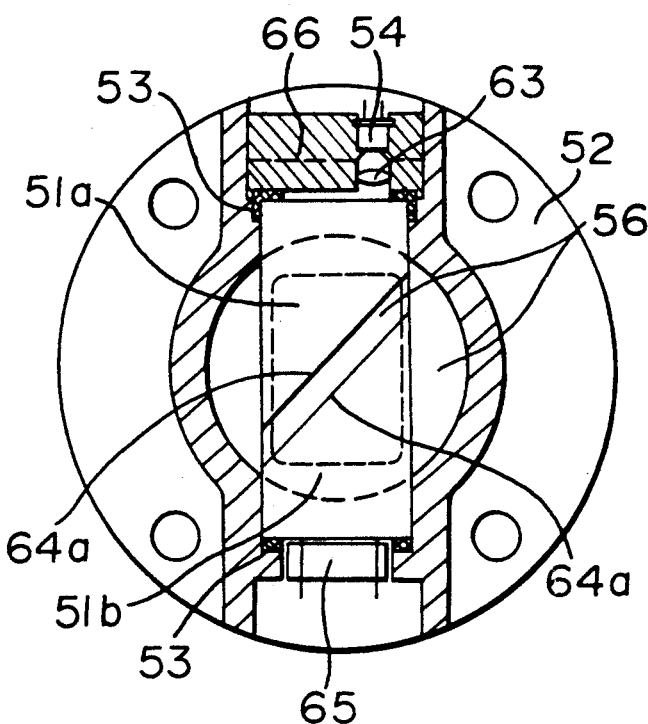

FIG. 4a is a structural diagram showing the detecting part of the alcoholic content detector according to one embodiment of the present invention, and FIG. 4b is a cross-sectional view taken along a line IV—IV in FIG. 4a. In both figures of drawing, a reference numeral 66 designates a holder for retaining the diaphragm 62, the light emitting element 54 and the lens 63; and a numeral 67 refers to a holder for the light transmission body. The light transmission body 51 is constructed with light transmitting members 51a and 51b, each having a refractive interface at one end thereof. The light transmitting member 51a has, at one end thereof, the light emitting element 54, and, at the other end thereof, the refractive interface 64a, while the light transmitting member 51b has, at one end thereof, the refractive interface 64b, and, at the other end thereof, the PSD 65. Each of the light transmitting members 51a and 51b is fixed to the holder 67 for the light transmitting member in such a manner that both refractive interfaces 64a and 64b may become parallel each other, and these refractive interfaces are inserted in the fuel passageway 56 in a manner to be in contact with the fuel. In this case, the parallel disposition of the above-mentioned refractive interfaces 64a, 64b and the fuel passageway 56 is effective for reducing the pressure loss. The light transmitting body 51 integrally connected with the holder 67 for the light transmitting body is insulated from the fuel side between the fuel seal 53 and the casing 52, the casing 52 being mounted in clamping through packing material, etc. on the piping at the high pressure side closer to the fuel injector 21.

Figure 5:
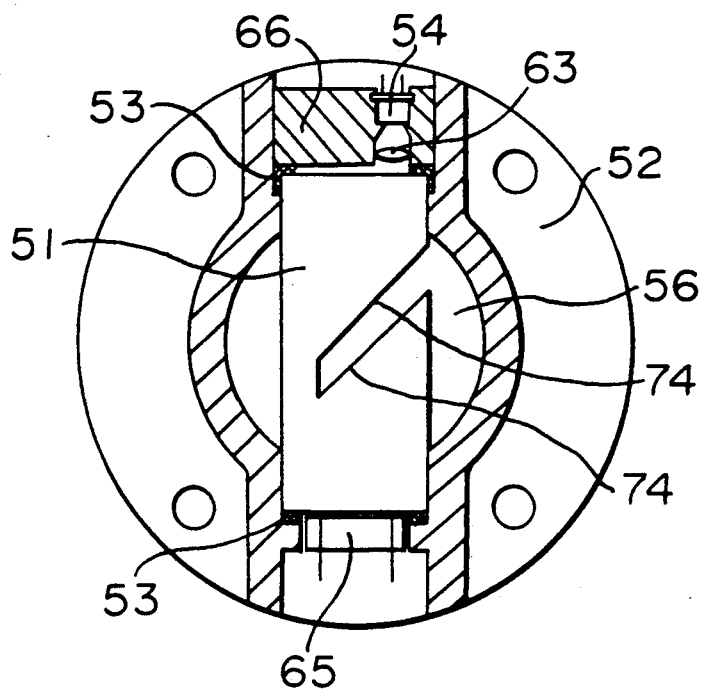
FIG. 5 is also a cross-sectional view, similar to FIG. 4b, of the sensing part of the alcoholic content detector according to another embodiment of the present invention.

FIG. 5 is a cross-sectional view of the detecting part according to another embodiment of the present invention, in which parallel grooves having a predetermined angle with respect to the axis are formed in an intermediate part of the light transmitting body 51, with both surfaces 74, 74 of the parallel grooves being made the refractive interfaces with the fuel. According to such construction, it will no longer be necessary to provide the holder 67 for the light transmitting body, which contributes to simplify the structure of the device with added precision in the distance between the refractive interfaces and the angle of the grooves with respect to the axis of the light transmission body.

In the above described embodiment of the present invention, the light transmitting body 51 has been shown in the form of a rectangular column, but it is not limited to this shape alone and any other forms such as circular column and so forth can be adopted for the purpose of the present invention. Further, it is sufficient that the refractive interface to be formed at an intermediate portion of the light transmission body be substantially parallel each other.

Figure 6:
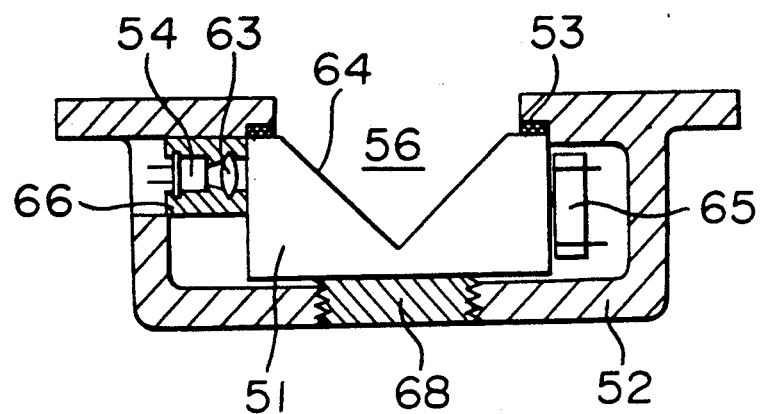
FIGS. 6 and 7 are respective cross-sectional views showing the sensing part of the alcoholic content detector according to still other embodiments of the present invention.
Figure 7:
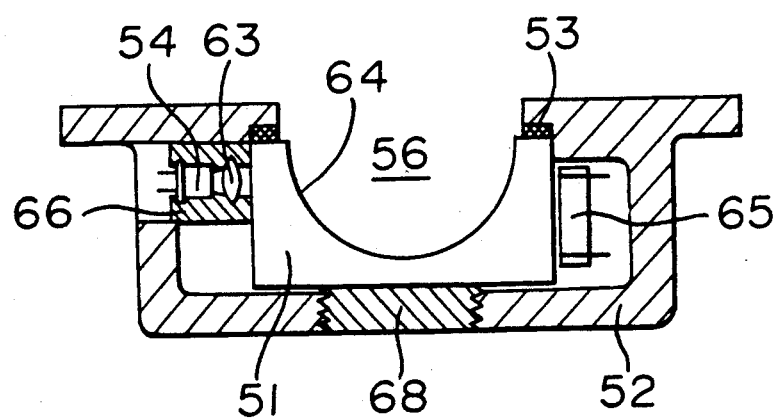

FIG. 6 is a cross-sectional view of the detection section according to still another embodiment of the present invention, in which a refractive interface 64 is formed by cutting out a part of the light transmission body 51 at a predetermined angle, or a conical refractive plane 64 having a predetermined apex angle is formed in the light transmission body 51. Such refractive planes can be formed by press-forming the light transmitting material and then polishing the thus pressformed surfaces. The light transmission body 51 is fixed to the casing 52 through the fuel seal 53 by means of pressing member 68. Since such construction does not require insertion into the fuel of the light transmission body 51, it can be simply mounted on the lateral surface of, for example, the fuel distribution pipe 26, and so forth, such that hardly any undesirable pressure loss can occur. Further, as shown in FIG. 7, such refractive interface to be in contact with the fuel may be made of a part of a circumferential surface formed by cutting out a part of the light transmission body in a cylindrical shape, or it may be made of a part of a spherical surface formed by cutting out a part of the light transmission body in a spherical shape.

It is noted that in the above described embodiments of the present invention, the light position sensing detector (PSD) has been used as an exemplary of the single dimensional light position detecting element 65. It will, however, be apparent to those persons skilled in the art that the similar effects can be expected by use of a photodiode array, CCD, and other position detecting elements. Furthermore, insulation of the light transmission body 51 from the fuel can be realized not by the fuel seal 53, but by filling the space between the light transmission body 51 and the casing 52 with sealing material, or by adhesion of these two members, or by metallizing the peripheral surface of the light transmission body 51, followed by welding, soldering, etc. of the metallized peripheral surface with the casing 52.

Furthermore, the above described embodiments of the detecting device according to the present invention are directed to the case in which the alcoholic content in the fuel is detected. It should, however, be noted that the detecting device of the present invention can also be used widely as the refractive index measuring device for other liquids.

As has so far been explained in detail, since the detecting device according to the present invention is so constructed that the refractive interfaces for the fuel to be detected are formed at the intermediate portion of the light transmission body, the light emitting element is provided on one end of the light transmitting body, and the single dimensional light position sensing detector is provided on the other end of the light transmission body, so as to enable the alcoholic content in the fuel to be detected on the basis of a light incident position on the single dimensional light position sensing detector, it becomes possible to reduce the overall size of the detecting device, and yet to dispose the detecting device at a position in the piping closer to the fuel injector. In this way, the alcoholic content in the fuel as ejected from the fuel injector can always be detected in a continuous manner without any delay whatsoever. Moreover, irrespective of change in temperature of the detection device, the alcoholic content can be detected with good precision.

Figure 8:
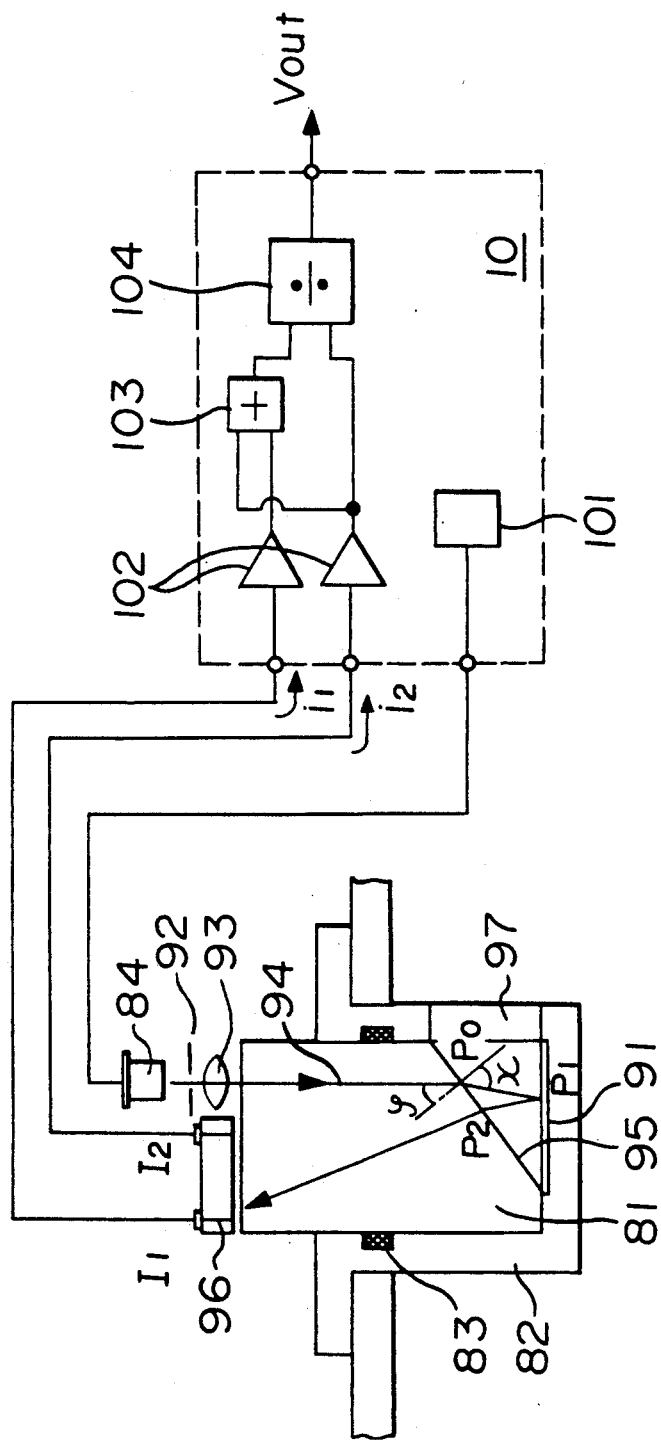
FIG. 8 is a schematic structural diagram showing the alcoholic content detector according to another embodiment of the present invention.

In the following, further explanations will be given as to other embodiments of the present invention in reference to FIG. 8 which shows schematically the structure of the alcoholic content detecting device. In the drawing, a reference numeral 81 designates the light transmission body of the same cylindrical shape as that used in the conventional alcoholic content detecting device, with the exception that one end of the cylindrical column is cut at a predetermined angle with respect to the axis of the cylinder, thereby forming the refractive interface 95. A numeral 91 refers to the reflecting surface, a numeral 92 refers to the diaphragm, a reference numeral 93 denotes the optical lens, a numeral 94 represents radiated light rays from the light emitting element 84, a numeral 96 designates the single dimensional light position detecting element which is the same semiconductor light position sensing detector (hereinafter abbreviated as "PSD") as shown in FIG. 2, and a numeral 97 refers to the fuel inlet port. A detection circuit 10 the same as that shown in FIG. 1 is composed of the constant current driving section 101 for driving the light emitting element 84, the pre-amplifier 102 for the photocurrent from the PSD 96, the adder 103, and the divider 104. When the light emitting element 84 disposed at one end of the light transmission body 81 is driven by the constant current driving section 101 and emits light, the radiated light rays 94 pass through the diaphragm 92, and, while they are being converged by the optical lens 93, enter into the refractive interface 95 at the other end of the light transmission body 81 from the point PO at an incident angle $\Phi$. Owing to the fact that the refractive interface 95 is in contact with the fuel which has flowed in from the fuel inlet port 97, the incident light 94 is refracted with a refractive angle x = arc SIN (Nd/Nf x SIN $\Phi$) due to a difference between the refractive index Nf of the fuel at the point PO and the refractive index Nd of the light transmission body 81. The light rays which have been refracted at the point PO at its angle of refraction x and transmitted in and through the fuel, are reflected at a point P1 on the above-mentioned reflecting surface 91, are transmitted again in and through the fuel, enter into a point P2 on the refractive interface 95 to be refracted in the light transmitting body 81 in accordance with a relational expression between the incident angle $\Phi$ and the refractive angle x, and finally reach the PSD 96 disposed on the same side as the light emitting element 24. The lens 93 has its focal length selected in such a manner that the radiated light rays 94 may be collected on the PSD 96. An explanation for the principle of detecting the light position on the PSD 96 will be dispensed with, since it is identical with that of the light position sensing detector as shown in FIG. 2. Also, the explanation concerning variations in the output voltage $V_{out}$ with respect to the methyl alcohol content in the fuel gasoline, as shown in FIG. 3, will apply to this embodiment.

Figure 9:
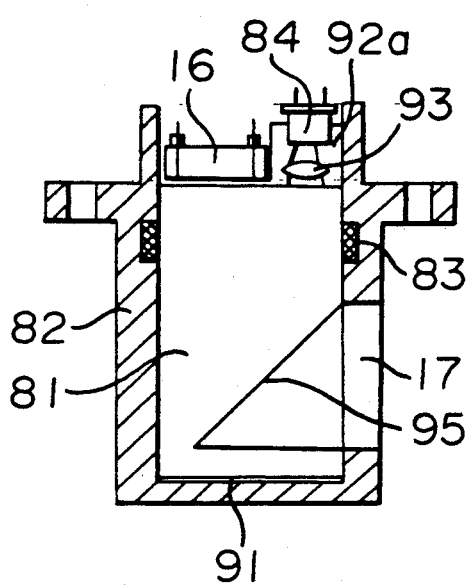
FIG. 9 is a cross-sectional diagram showing the sensing part of the alcoholic content detector according to the present invention.

FIG. 9 is a structural diagram showing the detection section of the alcoholic content detecting device, wherein a reference numeral 92a designates a holder having the retaining functions of the diaphragm 92, the light emitting element 84, and the lens 93. The light transmission body 81 has its refractive interface 95 formed by cutting its one end part in a wedge shape at a predetermined angle with respect to the axis of the cylinder, leaving a predetermined thickness there, while the reflecting surface 91 is formed on one end surface of the light transmission body 81 by vapor-deposition, etc. of metal thereon, thus making it a rear surface mirror. On the other hand, the light transmission body 81 is isolated from the fuel by means of the fuel seal 83 between it and the casing 82, the casing 82 being mounted on the high pressure side piping such as the fuel distribution pipe 26, etc., which is closer to the fuel injector 21, through a packing material or the like.

Figure 10:
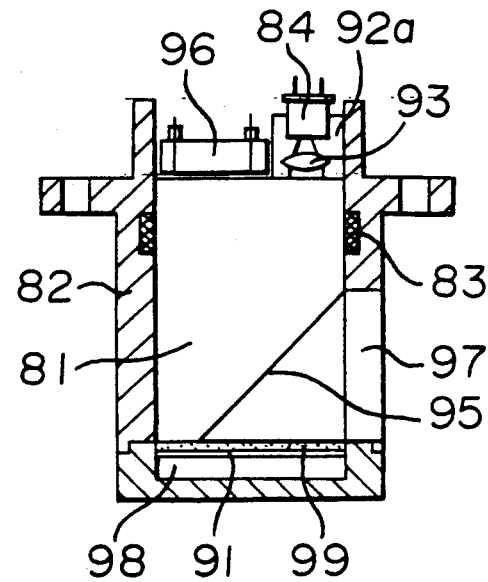
FIG. 10 is a cross-sectional view of the sensing part of the alcoholic content detector according to still another embodiment of the present invention.

FIG. 10 is also a structural diagram showing the detection section of the alcoholic content detecting device according to still another embodiment of the present invention, in which the reflecting surface 91 is formed by vapor-deposition of a metal film on the surface of a separate planar light transmission body 98, after which a light transmitting protective film 99 such as a thin film of plastic or ceramic material having oil-resistant properties is coated thereon to make it a front surface mirror. In this way, the light transmission body 81 has less surface to be polished, which leads to reduction in cost for the polishing work, with the consequence that the detecting section can be fabricated at a low manufacturing cost. Additionally, in this embodiment, the reflecting surface 91 is formed on the surface of the planar light transmission body 98, and, in the same manner, the reflecting surface 91 may also be formed on the rear surface of the light transmission body 81. In so doing, there is no necessity for the light transmitting protective film 99 to be provided.

Figure 11:
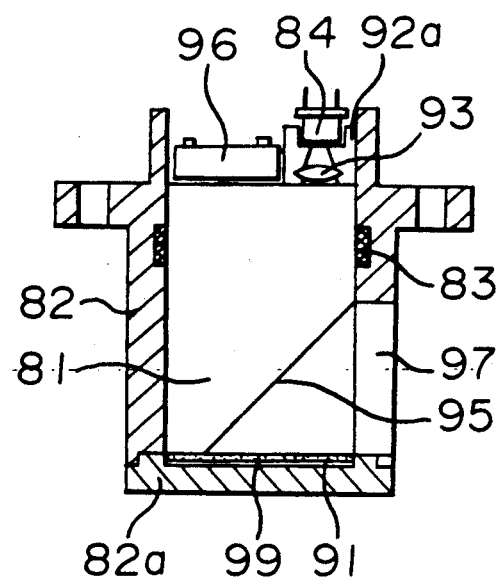
FIG. 11 is also a cross-sectional view of the sensing part of the alcoholic content detector according to a further object of the present invention.
Figure 12:
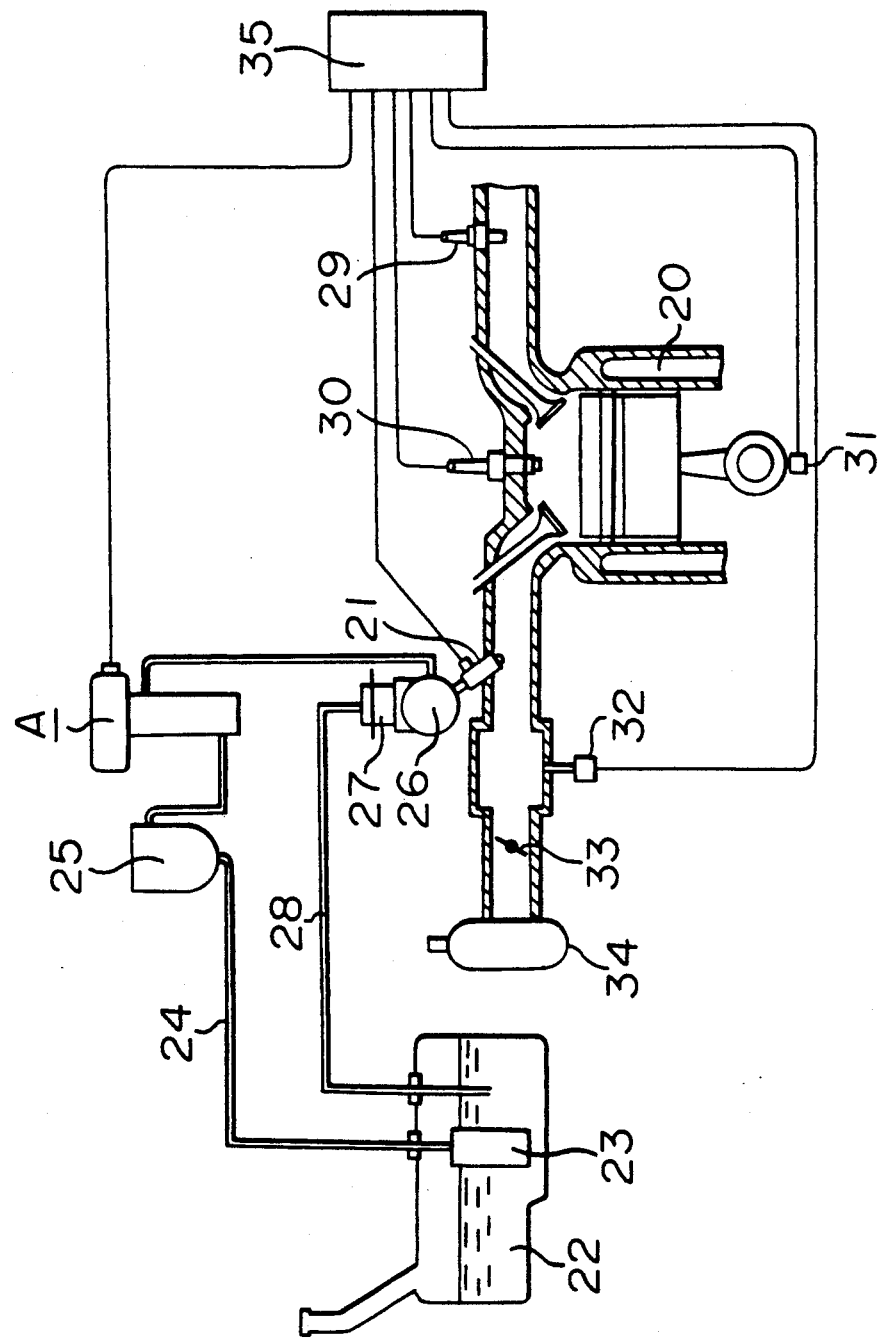
FIG. 12 is a schematic structural diagram showing a fuel control system provided with a conventional alcoholic content detector.

FIG. 11 is also a structural diagram showing the detecting section of the alcoholic content detecting device according to a further embodiment of the present invention, wherein the reflecting surface 91 is formed on the base member 82a of the casing 82. This reflecting surface 91 can be formed by surface polishing of the metallic base member 82a, or by laminating on this base member 82a other metallic films either by plating or by vapor-deposition. In so doing, the manufacturing cost of the detecting section can be further decreased by the reduction in number of the constituent parts, and, at the same time, the detection section can be made much smaller in size.

In each of the above described embodiments of the present invention, the light position sensing detector (PSD) has been used as one example of the single dimensional light position detecting element 96. It should, however, be apparent to those persons skilled in the art that the similar effect can be expected even by use of the light position detecting element such as a photodiode array CCD, and so forth. Furthermore, insulation of the light transmission body 81 from the fuel can be realized not by the fuel seal 83, but by filling the space between the light transmission body 81 and the casing 82 with sealing material, or by adhesion of these two members, or by metallizing the peripheral surface of the light transmission body 81, followed by welding, soldering, etc. of the metallized peripheral surface with the casing 82.

Furthermore, the above described embodiments of the detecting device according to the present invention are directed to the case, in which the alcoholic content in the fuel is detected. It should, however, be noted that the detecting device of the present invention can also be used widely as the refractive index measuring device for other liquids. As has so far been explained in detail in the foregoing, since the detecting device according to the present invention is so constructed that the light emitting element and the single dimensional light position detecting element are provided at one end of the light transmission body, and the refractive interface and the reflecting surface for the fuel to be detected are provided at the other end of the light transmitting body, it becomes possible to reduce the overall size of the detecting device, and yet to dispose the detecting device at a position of the piping which is closer to the fuel injector. On account of this, the alcoholic content in the fuel as ejected from the fuel injector can always be detected in a continuous manner without any delay whatsoever, and, moreover, irrespective of change in temperature of the detection device, the alcoholic content can be detected with good precision.

We claim:

1. A device for detecting alcoholic content in a fuel by finding its refractive index, said device having a surface for detecting the refractive index of the fuel and which constitutes a part of a fuel passageway, said device being disposed in a fuel supply pipe to an internal combustion engine and positioned proximate to said engine, characterized in that a light emitting element and a single dimensional light position sensing detector are provided at one end of a column-like transmission body, and a refractive interface and an oil-resistant reflecting surface are provided at the other end of said light transmission body so that a space between said refractive interface and said oil-resistant reflecting surface provides a part of the fuel passageway, wherein an incident light, which has entered into the refractive interface from the light emitting element and has been refracted there, is reflected at the oil-resistant reflecting surface, after which said reflected light is again caused to enter into the refractive interface, and then is collected on the single dimensional light position sensing detector, whereby a change in an angle of refraction of the light, due to the light being refracted twice is detected as a change in the position where the light is collected, on said single dimensional position sensing detector.

2. The device for detecting alcoholic content according to claim 1, wherein said oil-resistant reflecting surface is a rear surface mirror formed by coating a reflecting layer on the other end surface, opposing said refractive interface, of said column-like light transmission body with respect to said light emitting element.

3. The device for detecting alcoholic content according to claim 1, wherein said reflecting surface is a rear surface mirror formed by coating a reflecting layer on a back surface, opposite the surface in contact with the fuel, of a separate planar light transmission body which is disposed at the other end surface of said column-like light transmission body so as to oppose said refractive interface.

4. The device for detecting alcoholic content according to claim 1, wherein said oil-resistant reflecting surface is a front surface mirror which comprises a reflecting film formed on a substrate and a light transmitting protective film having oil-resistant properties and being formed on said reflecting film, said substrate being disposed at the other end of said column-like light transmission body so as to oppose said refractive interface.

* * * * *